(12) United States Patent
Yang et al.

(10) Patent No.: US 11,781,186 B2
(45) Date of Patent: Oct. 10, 2023

(54) KIT FOR AFLATOXIN B1 (AFB1) MONITORING

(71) Applicant: QINGDAO AGRICULTURAL UNIVERSITY, Qingdao (CN)

(72) Inventors: Qingli Yang, Qingdao (CN); Qi Wang, Qingdao (CN); Wei Wu, Qingdao (CN); Fangyuan Zhao, Qingdao (CN); Xiudan Hou, Qingdao (CN); Haiyan Zhao, Qingdao (CN); Yinglian Zhu, Qingdao (CN); Zhaojie Li, Qingdao (CN)

(73) Assignee: QINGDAO AGRICULTURAL UNIVERSITY, Shandong (CN)

( * ) Notice: Subject to any disclaimer, the term of this patent is extended or adjusted under 35 U.S.C. 154(b) by 329 days.

(21) Appl. No.: 17/154,280

(22) Filed: Jan. 21, 2021

(65) Prior Publication Data
US 2022/0213545 A1    Jul. 7, 2022

(30) Foreign Application Priority Data
Jan. 7, 2021 (CN) ............................ 202110015995

(51) Int. Cl.
*C12N 15/11* (2006.01)
*C12Q 1/6876* (2018.01)
*C12N 15/115* (2010.01)

(52) U.S. Cl.
CPC .......... *C12Q 1/6876* (2013.01); *C12N 15/115* (2013.01); *C12N 2310/16* (2013.01)

(58) Field of Classification Search
CPC .............. C12N 15/115; C12N 2310/16; G01N 21/6428; G01N 21/6486; G01N 27/3278
See application file for complete search history.

(56) References Cited

U.S. PATENT DOCUMENTS

2012/0225494 A1* 9/2012 Le ...................... C12N 15/1048
536/23.1

FOREIGN PATENT DOCUMENTS

| CN | 104840966 A | 8/2015 |
|---|---|---|
| CN | 110031441 A | 7/2019 |
| CN | 110441277 A | 11/2019 |
| CN | 110455764 A | 11/2019 |
| WO | 2017075696 A1 | 5/2017 |
| WO | 2018029228 A1 | 2/2018 |

OTHER PUBLICATIONS

Pei et al., A DNA nanostructure-based biomolecular probe carrier platform for electrochemical biosensing, Advanced Materials, vol. 22, pp. 4754-4758. (Year: 2010).*

Qu et al., Highly efficient fluorescence sensing of kanamycin using Endo IV-powered DNA walker and hybridization chain reaction amplification, Microchimica Acta, vol. 187:193, pp. 1-8. (Year: 2020).*

Deng et al., A ratiometric fluorescent biosensor based on cascaded amplification strategy for ultrasensitive detection of kanamycin, Sensors and Actuators B: Chemical, vol. 273, pp. 1495-1500. (Year: 2018).*

Junhua Chen et al., "An enzyme-free catalytic DNA circuit for amplified detection of aflatoxin B1 using gold nanoparticles as colorimetric indicators" Nanoscale, 2016, 8, 9791-9797 (Jan. 1, 2016).

Qi Wang et al., "Graphene oxide quantum dots based nanotree illuminates AFB1: Dual signal amplified aptasensor detection AFB1" Sensors & Actuators: B. Chemical 345 (2021) 130387 (Jun. 30, 2021).

Seyed Mohammad Taghdisi et al., "Novel Colorimetric Aptasensor for Zearalenone Detection Based on Nontarget-Induced Aptamer Walker, Gold Nanoparticles, and Exonuclease-Assisted Recycling Amplification" ACS Appl. Mater. Interfaces 2018, 10, 12504-12509 (Mar. 22, 2018).

Xinsheng Yang et al., "Portable Aptasensor of Aflatoxin B1 in Bread Based on a Personal Glucose Meter and DNA Walking Machine" ACS Sensors, vol. 3, No. 7, pp. 1368-1375 (Jul. 27, 2018).

Yongmei Jia et al., "Recent Development of Aptamer Sensors for the Quantification of Aflatoxin B1" Appl. Sci. 2019, 9, 2364; doi:10.3390/app9112364 (Jan. 1, 2019).

\* cited by examiner

*Primary Examiner* — Dana H Shin
(74) *Attorney, Agent, or Firm* — SZDC LAW P.C.

(57) ABSTRACT

The invention displays aflatoxin $B_1$ ($AFB_1$) detection kit and $AFB_1$ detection method. The invention belongs to the technical field of detecting harmful substances. The $AFB_1$ detection kit was fabricated with DNA walker structure, endonuclease, hairpin H1 and H2. The $AFB_1$ detection kit has benefits of high sensitivity and short detection time based on signal amplification strategy of DNA Walker structure and hyperbranched fluorescent nanotrees. The present invention can realize high sensitive and rapid detection of $AFB_1$.

4 Claims, 2 Drawing Sheets

Specification includes a Sequence Listing.

SEQUENCE LISTING

<160> NUMBER OF SEQ ID NOS: 8

<210> SEQ ID NO 1
<211> LENGTH: 47
<212> TYPE: DNA
<213> ORGANISM: Artificial sequence
<220> FEATURE:
<223> OTHER INFORMATION: Aflatoxin B1

<400> SEQUENCE: 1
gttgggcacg tgttgtctct ctgtgtctcg tgcccttcgc taggccc      47

<210> SEQ ID NO 2
<211> LENGTH: 45
<212> TYPE: DNA
<213> ORGANISM: Artificial sequence
<220> FEATURE:
<223> OTHER INFORMATION: Aflatoxin B1

<400> SEQUENCE: 2 ttttttttt tttttttttt tagacaacac gtgcccaacg gagac      45

-continued

```
<210> SEQ ID NO 3
<211> LENGTH: 88
<212> TYPE: DNA
<213> ORGANISM: Artificial sequence
<220> FEATURE:
<223> OTHER INFORMATION: Aflatoxin B1

<400> SEQUENCE: 3
gtctccgttt caagcgcagc acttacctgt atcctttccg agttacgtct gtccctagag    60
ttttcctact tacaagagcc ggatacgc                                       88

<210> SEQ ID NO 4
<211> LENGTH: 105
<212> TYPE: DNA
<213> ORGANISM: Artificial sequence
<220> FEATURE:
<223> OTHER INFORMATION: Aflatoxin B1

<400> SEQUENCE: 4
tcagtctagg attcggcgtg ggttttttgga tacaggtaag tgctgcgctt gtttaatgga   60
acttgagatg ttagggagtt ttcttagcta ggtgtgatac attac                    105

<210> SEQ ID NO 5
<211> LENGTH: 105
<212> TYPE: DNA
<213> ORGANISM: Artificial sequence
<220> FEATURE:
<223> OTHER INFORMATION: Aflatoxin B1

<400> SEQUENCE: 5
tcagtctagg attcggcgtg ggttttttat caccaggcag ttgacagtgt atttctccct    60
aacatctcaa gttccatttt tgcgtatccg gctcttgtaa gtagg                    105

<210> SEQ ID NO 6
<211> LENGTH: 105
<212> TYPE: DNA
<213> ORGANISM: Artificial sequence
<220> FEATURE:
<223> OTHER INFORMATION: Aflatoxin B1

<400> SEQUENCE: 6
tcagtctagg attcggcgtg ggttttttac actgtcaact gcctggtgat atttactcta    60
gggacagacg taactcggtt tgtaatgtat cacacctagc taaga                    105

<210> SEQ ID NO 7
<211> LENGTH: 60
<212> TYPE: DNA
<213> ORGANISM: Artificial sequence
<220> FEATURE:
<223> OTHER INFORMATION: Aflatoxin B1

<400> SEQUENCE: 7
gcgtgggttg cgctgatcaa gactccatga aacccacgcc gaatcctaga ctgagcgctg    60

<210> SEQ ID NO 8
<211> LENGTH: 60
<212> TYPE: DNA
<213> ORGANISM: Artificial sequence
<220> FEATURE:
<223> OTHER INFORMATION: Aflatoxin B1

<400> SEQUENCE: 8
tcatggagtc ttgatcagcg caacccacga cagcgctcag tctaggattc ggcgtgggtt    60
```

KIT FOR AFLATOXIN B1 (AFB1) MONITORING

CROSS-REFERENCE TO RELATED APPLICATION

The present disclosure claims the priority to the Chinese patent application with the filing number 202110015995.9, filed with the Chinese Patent Office on Jan. 7, 2021, and entitled "A kit for aflatoxin B1 (AFB1) monitoring, preparation and detection method thereof", which is incorporated herein by reference in its entirety.

TECHNICAL FIELD

The invention displays an aflatoxin $B_1$ ($AFB_1$) detection kit and a $AFB_1$ detection method. The invention belongs to the technical field of detecting harmful substances.

BACKGROUND ART $AFB_1$ is low-molecular-weight natural secondary metabolites produced by *Aspergillus flavus* and *Aspergillus parasiticus*. $AFB_1$ is the most toxic among all mycotoxins, posing teratogenic, carcinogenic, and mutagenic risks to humans, and has been labeled as a group I carcinogen in humans by the International Agency for Research on Cancer (IARC). Given the serious impact of this mycotoxin on human health, governments and relevant organizations have formulated strict regulations and testing methods to limit the level of aflatoxin in food.

Traditionally, the most widely used mycotoxin analysis techniques include high performance liquid chromatography (HPLC), gas chromatography/mass spectrometry (GC/MS) and probe-based enzyme-linked immunoassay (ELISA). Instrumental analysis methods need high cost instruments and equipment, long test times, and skilled lab researchers for the detection process. In addition, traditional ELISA requires time-consuming culture and specific elution conditions, and the enzymes involved in the experiment are prone to denaturation or inactivation. Therefore, it is urgent to carry out in-depth research in this field and establish a rapid and effective method for the separation and detection of $AFB_1$ in food.

Aptamers are short, single-stranded oligonucleotide sequences (DNA, RNA, or nucleic acid analogs) selected from a nucleic acid molecular library using the in vitro systematic evolution of ligands by exponential enrichment (SELEX) method. Like antibodies, aptamers have strict recognition and high affinity for binding ligands. Because of its advantages of easy synthesis, easy storage and easy modification, it has a wide application prospect in analysis and detection.

DNA nanostructures are assembled from single strand DNA through complementary base pairs, which have high controllability, biocompatibility and stability. In recent years, DNA nanostructures have been increasingly used in the construction of biosensors. DNA nanostructures have many functions, such as drug delivery, signal carrying, signal amplification and rigid support, which greatly improve the performance of biosensors.

SUMMARY

In view of the problems in the prior art, the purpose of the present invention is to provide a kit for detecting $AFB_1$ and a method for detecting $AFB_1$. The kit of the invention realizes dual signal amplification based on DNA Walker structure and hyperbranched fluorescent nanotree structure. This method not only enhances the detection signal of $AFB_1$ and improves the reaction speed, but also realizes the high sensitive and rapid detection of $AFB_1$.

In order to achieve the above purpose, the invention adopts the following technical scheme:

A detection kit for $AFB_1$, which contains DNA walker structure, endonuclease, hairpin H1 and H2.

The DNA Walker structure is gold nanoparticles (AuNPs) modified with WA double strand and DNA tetrahedrons (DTNs).

The WA is a double stranded structure composed of aptamer A of $AFB_1$ and its partially complementary nucleic acid sequence W.

The sequence E1 on the W chain and the sequence E2 on the S1 chain can form the recognition site of endonuclease by base complementary pairing.

There is a 4-15 base sequence E1 in the nucleic acid sequence W and A are not complementary. The nucleic acid sequence at the junction of DTNs and gold nanoparticles contains a 4-15 base sequence E2. The sequence E1 on the W chain and the sequence E2 on the S1 chain can form the recognition site of endonuclease by base complementary pairing.

Both ends of the hairpin structure H1 are respectively modified with a fluorescent group and a fluorescence quenching group.

The DTNs are self-assembled by four DNA single strands through base complementary. The nucleic acid sequence of DTNs pivot is complementary to the partial sequence of hairpin structure H1, which is used to open the hairpin structure of H1. The hairpin structure H1 is complementary to the partial sequence base of hairpin structure H2, which is used to open the hairpin structure of H2.

On the basis of the above scheme, the cutting endonuclease is Nt.BsmAI.

On the basis of the above scheme, the sequence of aptamer A of $AFB_1$ is shown in SEQ ID NO:1.

On the basis of the above scheme, the nucleic acid sequence of W is shown in sequence ID NO:2. The 5'end of W is modified by sulfhydryl group.

On the basis of the above scheme, the four DNA single stranded sequences of the DTNs are shown in the sequence of SEQ ID NO:3-6. The 5' end of the sequence ID NO:3 is modified by sulfhydryl group.

On the basis of the above scheme, the nucleic acid sequence of the H1 is shown in SEQ ID NO:7.

On the basis of the above scheme, the fluorescent group in the H1 is FAM fluorescent group, and the fluorescence quenching group is Dabcyl.

On the basis of the above scheme, the nucleic acid sequence of the H2 is shown in SEQ ID NO:8.

On the basis of the above scheme, DNA Walker structure is prepared in the following steps:

Thiol groups of WA and DTNs were reduced by TCEP for 30 min. The activated WA and DTNs were mixed in a molar ratio of 1:4, and then 0.1% AuNPs solution was added to the mixture at 4° C. overnight. Next, 1M sodium chloride solution was added to the above solution every 1 h for a total of 5 times to ensure that the final concentration of sodium chloride is 0.15 M. After each addition of sodium chloride, the solution needs to be sonicated for 10 s. Finally, the uncoupled WA and DTNs were removed by centrifugation to obtain the DNA walker structure.

The steps for using the above kit to detect $AFB_1$ are as follows:

(1) The test sample solution and DNA walker solution were mixed at 37° C. and incubated for 0.5 h. Then the cutting endonuclease Nt.BsmAI was added under 37° C. for 0.5 h. Then the mixture was kept at 65° C. for 20 min.

(2) Adding sodium chloride solution to the solution after reaction in step (1), the AuNPs was precipitated in the salt solution to retain the supernatant.

(3) H1 and H2 were added to above solution (2) for the reaction at 37° C. for 15 min. The molar ratio of H1 and H2 was 1:1.

(4) The fluorescence intensity of the solution after reaction in step (3) was detected at 490 nm excitation wavelength. The measured fluorescence intensity was introduced into the standard curve.

When the kit of the invention detects $AFB_1$ in the sample, the adopted sample solution needs to be a clear and transparent liquid.

The advantages of the technical scheme of the invention are as follows:

The DNA Walker structure of the invention is a signal amplification structure mediated by the target $AFB_1$. DTNs not only concatenate the DNA Walker structure and the hyperbranched fluorescent nanotree, but also provide multiple vertex for hyperbranched fluorescent nanotree. The invention accelerates the reaction speed and realize the dual amplification of signal.

The method of the invention has the characteristics of low detection cost, fast detection and low requirements for detection instruments.

In particular, the invention first uses DNA Walker structure, DNA tetrahedron structure and hyperbranched fluorescent nanotree as signal amplification means to detect mycotoxins. The invention can improve the sensitivity of aptasensor and provide a new technology for rapid screening of mycotoxin contamination in food.

DETAILED DESCRIPTION OF THE INVENTION

Figure 1:
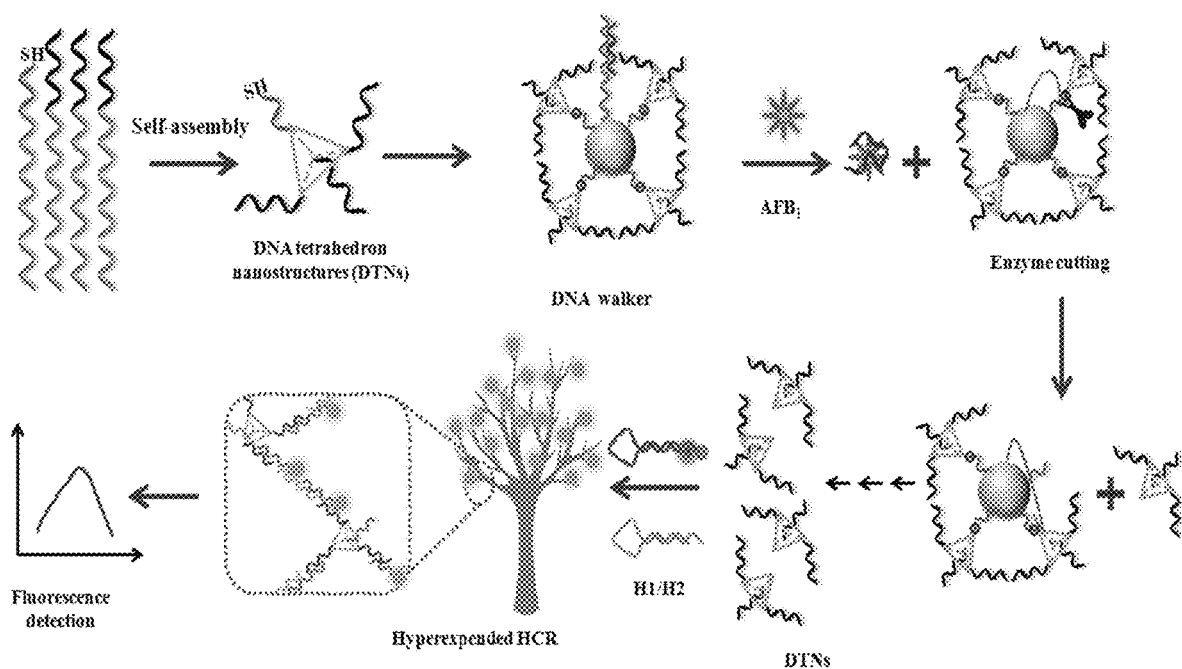
FIG. 1: Schematic diagram of detection principle of the method of the invention.

Unless otherwise specified, the terms used in the description of the invention typically have the meanings commonly appreciated by those ordinarily skilled in the art.

The invention is further detailed below in combination with embodiments and reference data. The following embodiments are only used for illustratively explaining the invention, and are not intended to limit the scope of the invention in any form.

Embodiment 1

The detection principle of the invention is as follows:
DTNs are formed by complementary self-assembly of S1, S2, S3 and S4. There is a single strand extension sequence at the four vertices of DTNs. WA double stranded structure composed of aptamer A of $AFB_1$ and its partially complementary nucleic acid sequence W. The 5'end of S1 and W chain were modified by sulfhydryl group. After thiol reduction by TCEP reductant, DTNs and WA were modified on the surface of AuNPs to form DNA Walker structure.

In the presence of $AFB_1$, aptamer A combined with $AFB_1$ and dissociated from AuNPs with DNA Walker structure. Subsequently, the W chain was in a single chain state and began to swim on the surface of AuNPs driven by base complementation. The binding of E1 on W chain with E2 on S1 forms the recognition site of endonuclease, which triggers the cleavage of S1 chain by endonuclease and makes DTN dissociate from the surface of AuNPs. W would swim to the next binding site until the DTNs are cut down to complete the first amplification of the signal.

The nucleic acid sequence of DTNs is complementary to the partial sequence of hairpin H1, resulting in the opening of hairpin H1. The extended sequence of H1 is complementary to the partial sequence of H2, resulting in the opening of the hairpin structure of H2. These processes lead to chain reaction and further construct hyperbranched nanostructures. Both ends of the hairpin structure H1 are respectively modified with a fluorescent group and a fluorescence quenching group. In the open H1, the fluorescence group and the fluorescence quenching group are separated, so that the fluorescence is restored. With the continuous opening of H1 and H2, the fluorescence signal brought by FAM is also expanding, completing the second signal amplification. $AFB_1$ was determined by fluorescence intensity.

A detection kit for $AFB_1$, which contains DNA walker structure, endonuclease, hairpin H1 and H2.

The DNA walker structure is prepared by the following method:

(1) Self-Assembly of DTNs

The four ssDNAs were mixed equivalently in buffer (10 mM Tris-HCl, 2.5 mM MgCl2, 100 mM NaCl pH 8.0), and the mixture was heated at 95° C. for 5 min, 45° C. for 30 min. Finally, the assembled DTNs were purified by 3% agarose gel electrophoresis.

(2) Hybridization Between W and A

The W and A were mixed equivalently, and the mixture was heated at 95° C. for 5 min and then slowly cooled to 25° C.

(3) Assembly of DNA Walker Structure

Thiol groups of WA and DTNs were reduced by TCEP for 30 min. The activated WA and DTNs were mixed in a molar ratio of 1:4, and then 0.1% AuNPs solution was added to the mixture at 4° C. overnight. Next, 1M sodium chloride solution was added to the above solution every 1 h for a total of 5 times to ensure that the final concentration of sodium chloride is 0.15 M. After each addition of sodium chloride, the solution needs to be sonicated for 10 s. Finally, the uncoupled WA and DTNs are removed by centrifugation to obtain the DNA walker structure.

The above sequence is shown in the following table:

| Name | Sequence (5'-3') | Number |
| --- | --- | --- |
| A | GTTGGGCACGTGTTGTCTCTCTGTGTCTCG TGCCCTTCGCTAGGCCC | SEQ ID NO: 1 |
| W | SH-TTTTTTTTTTTTTTTTTTTTAGACAA CACGTGCCCAACGGAGAC | SEQ ID NO: 2 |
| S1 | SH-GTCTCC\*GTTTCAAGCGCAGCACTTAC CTGTATCCTTTCCGAGTTACGTCTGTCCCT AGAGTTTTCCTACTTACAAGAGCCGGATAC GC | SEQ ID NO: 3 |

-continued

| Name | Sequence (5'-3') | Number |
|------|------------------|--------|
| S2 | TCAGTCTAGGATTCGGCGTGGGTTTTTGGA TACAGGTAAGTGCTGCGCTTGTTTAATGGA ACTTGAGATGTTAGGGAGTTTTCTTAGCTA GGTGTGATACATTAC | SEQ ID NO: 4 |
| S3 | TCAGTCTAGGATTCGGCGTGGGTTTTTAT CACCAGGCAGTTGACAGTGTATTTCTCCCT AACATCTCAAGTTCCATTTTTGCGTATCCG GCTCTTGTAAGTAGG | SEQ ID NO: 5 |
| S4 | TCAGTCTAGGATTCGGCGTGGGTTTTTAC ACTGTCAACTGCCTGGTGATATTTACTCTA GGGACAGACGTAACTCGGTTTGTAATGTAT CACACCTAGCTAAGA | SEQ ID NO: 6 |
| H1 | FAM-GCGTGGGTTGCGCTGATCAAGACTCC ATGA AACCCACGCCGAATCCTAGACTGAGC GCTG-Dabcyl | SEQ ID NO: 7 |
| H2 | TCATGGAGTCTTGATCAGCGCAACCCACGA CAGCGCTCAGTCTAGGATTCGGCGTGGGTT | SEQ ID NO: 8 |

The sequence of single underline in the above table is the complementary sequence of A and W. The double underlined sequences are S2, S3, S4 and the complementary sequences of H1 and H2. The bold sequence represents E1 on the w Chain and E2 on the S1 chain. * is the cleavage site of endonuclease.

Embodiment 2

Method for detecting $AFB_1$ using the kit of embodiment 1:

(1) The sample solution was filtered and diluted 10 times. The 10 μL test sample solution and DNA walker solution were mixed at 37° C. and incubated for 0.5 h. Then the cutting endonuclease Nt.BsmAI was added under 37° C. for 0.5 h. The mixture was kept at 65° C. for 20 min.

(2) Adding sodium chloride solution to the solution after reaction in step (1), the AuNPs is precipitated in the salt solution to retain the supernatant.

(3) H1 and H2 were added to above solution (2) for the reaction at 37° C. for 15 min. The molar ratio of H1 and H2 was 1:1.

(4) The fluorescence intensity of the solution after reaction in step (3) was detected at 490 nm excitation wavelength. The measured fluorescence intensity was introduced into the standard curve.

Sensitivity of the Kit of Embodiment 1

Figure 2:
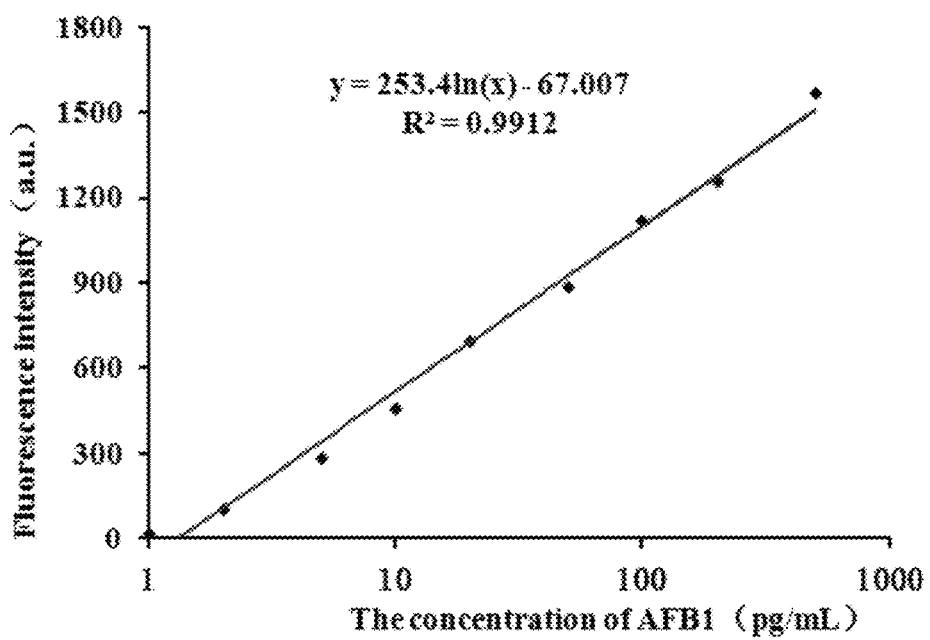
FIG. 2: The sensitivity detection of the detection kit.

Different concentrations of $AFB_1$ were used to test the sensitivity of the test kit in embodiment 1 of the present invention by the test method in embodiment 2. The $AFB_1$ of different concentration gradients were 1, 2, 5, 10, 20, 50, 100, 200, 500 pg/mL. As shown in FIG. 2, the relationship between $AFB_1$ concentration and fluorescence intensity was $y=253.4 \ln(x)-67.007$, $R^2=0.9912$. The detection range of embodiment 1 kit was 1-500 pg/mL, and the detection limit was 0.5 pg/mL.

The Specificity Detection of the Kit of Embodiment 1

Figure 3:
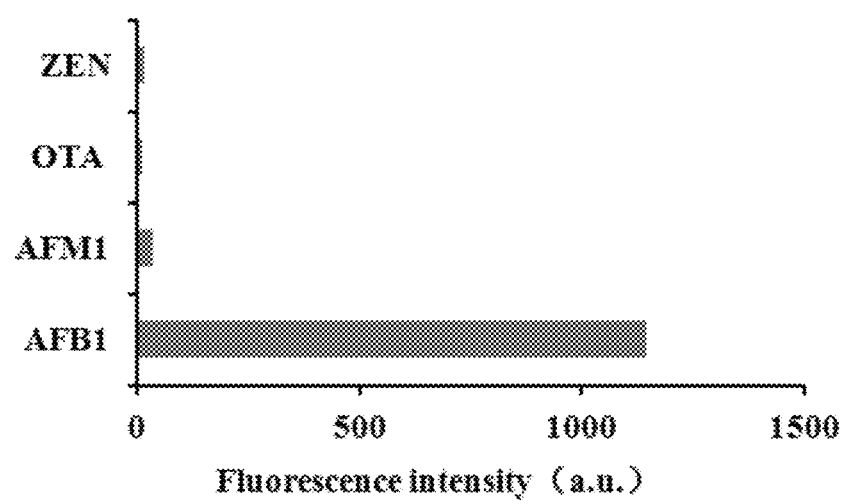
FIG. 3: The specificity detection of the detection kit.

The specificity of the kit was further checked using other possible interfering mycotoxins, such as aflatoxin M1 ($AFM_1$), zearalenone (ZEN) and ochratoxin A (OTA). The concentration of each toxin was 100 pg/mL. The specific results are shown in FIG. 3. The value of $AFB_1$ is significantly higher than that of other mycotoxins. Therefore, the kit of embodiment 1 of the invention has high specificity for $AFB_1$.

The embodiments are only preferred ones of the invention, and are not intended to limit the invention in any form. Any skilled in the art can transform or modify the technical contents disclosed below to obtain equivalent embodiments. Any simple modifications or equivalent transformations to the following embodiments according to the technical essence of the invention without deviating from the contents of the technical solutions of the invention should also fall within the protection scope of the technical solutions of the invention.

The invention claimed is:

1. A detection kit for $AFB_1$ (Aflatoxin $B_1$), comprising:
   a DNA walker structure;
   an endonuclease;
   a first hairpin structure H1; and
   a second hairpin structure H2,
   wherein the DNA Walker structure comprises gold nanoparticles (AuNPs) modified with a WA double strand and DNA tetrahedrons (DTNs);
   wherein the WA double strand is a double stranded structure consisting of an aptamer A of $AFB_1$ and a partially complementary nucleic acid sequence W;
   wherein the aptamer A of $AFB_1$ comprises a sequence set forth in SEQ ID NO:1;
   wherein the partially complementary nucleic acid sequence W comprises a sequence set forth in SEQ ID NO:2, and a 5' end of the partially complementary nucleic acid sequence W is modified by a sulfhydryl group;
   wherein a sequence E1 on the partially complementary nucleic acid sequence W and a sequence E2 on a S1 chain of the DTNs form a recognition site of the endonuclease by base complementarity pairing;
   wherein the sequence E1 is a 6-base sequence at the 3' end of the sequence set forth in SEQ ID NO:2 complementary nucleic acid sequence W are not complementary, and a junction of the DTNs and the AuNPs comprises the sequence E2;
   wherein both ends of the first hairpin structure H1 are modified with a fluorescent group and a fluorescence quenching group, respectively;
   wherein the DTNs are self-assembled by four DNA single strands S1, S2, S3, and S4 through base complementary, the four DNA single strands S1, S2, S3, and S4 comprise the sequences set forth in SEQ ID NOs:3-6, respectively, and a 5' end of SEQ ID NO:3 is modified by sulfhydryl group;
   wherein the sequence E2 is a 6-base sequence at the 5' end of the sequence set forth in SEQ ID NO:3; and
   wherein the DTNs are partially complementary to the first hairpin structure H1, the DTNs are used to open the first hairpin structure of H1, and the first hairpin structure H1 comprises the sequence set forth in SEQ ID NO:7; the first hairpin structure H1 is partially complementary to the hairpin structure H2, the first hairpin structure H1 is used to open the second hairpin structure of H2, and the second hairpin structure H2 comprises the sequence set forth in SEQ ID NO:8.

2. The detection kit for $AFB_1$ according to claim 1, wherein the endonuclease is endonuclease Nt.BsmAI.

3. The detection kit for $AFB_1$ according to claim 1, wherein the fluorescent group is an FAM (fluorescein amidites) fluorescent group, and the fluorescence quenching group is Dabcyl (4-(4'-dimethylaminophenylazo)benzoic acid).

4. The detection kit for $AFB_1$ according to claim 1, wherein the DNA walker structure is prepared by a method comprising the following steps:
   reducing thiol groups of the WA double strand and the DTNs by TCEP (tris carboxy ethyl phosphene) for 30 minutes;
   mixing the WA double strand and the DTNs in a molar ratio of 1:4;
   adding a 0.1% AuNPs solution to the mixture of the WA double strand and the DTNs at 4° C. overnight;
   adding 1M sodium chloride solution to the mixture every 1 hour for a total of 5 times to ensure that a final concentration of sodium chloride is 0.15 M, and after each addition of sodium chloride, sonicating the mixture for 10 seconds; and
   removing uncoupled WA double strand and DTNs by centrifugation to obtain the DNA walker structure.

* * * * *